(12) United States Patent
Brockman et al.

(10) Patent No.: US 11,963,866 B2
(45) Date of Patent: Apr. 23, 2024

(54) DEVICE FOR SECURING AN INTRAOCULAR DEVICE IN AN EYE

(71) Applicant: Brockman-Hastings LLC, Lexington, KY (US)

(72) Inventors: Edward Britt Brockman, Louisville, KY (US); Jeffrey Todd Hastings, Lexington, KY (US); Carlos Andres Jarro, Lexington, KY (US); James L. Russell, Lexington, KY (US)

(73) Assignee: Brockman-Hastings LLC, Lexington, KY (US)

( * ) Notice: Subject to any disclaimer, the term of this patent is extended or adjusted under 35 U.S.C. 154(b) by 0 days.

(21) Appl. No.: 17/136,833

(22) Filed: Dec. 29, 2020

(65) Prior Publication Data
US 2021/0228334 A1 Jul. 29, 2021

Related U.S. Application Data

(60) Provisional application No. 62/967,187, filed on Jan. 29, 2020.

(51) Int. Cl.
| | |
|---|---|
| *A61F 2/14* | (2006.01) |
| *A61B 5/00* | (2006.01) |
| *A61B 5/03* | (2006.01) |
| *A61B 5/1455* | (2006.01) |
| *A61F 2/16* | (2006.01) |
| *A61F 9/00* | (2006.01) |

(52) U.S. Cl.
CPC .............. *A61F 2/16* (2013.01); *A61B 5/03* (2013.01); *A61B 5/14555* (2013.01); *A61B 5/4839* (2013.01); *A61B 5/6821* (2013.01); *A61B 5/6883* (2013.01); *A61F 2/14* (2013.01); *A61B 2562/0247* (2013.01); *A61F 2002/1681* (2013.01); *A61F 2002/16902* (2015.04); *A61F 2002/16903* (2015.04); *A61F 9/0017* (2013.01); *A61F 2220/0008* (2013.01)

(58) Field of Classification Search
CPC .. A61F 2/16; A61F 2002/16903; A61B 3/117; A61B 3/00; A61B 3/10; A61B 3/1173; A61B 3/13; A61B 3/14; A61B 3/16; A61B 3/165; A61B 3/18; A61B 3/185
See application file for complete search history.

(56) References Cited

U.S. PATENT DOCUMENTS

| | | | |
|---|---|---|---|
| 6,193,656 B1 | 2/2001 | Jeffries et al. | |
| 6,770,093 B2 | 8/2004 | Worst et al. | |
| 7,435,259 B2 | 10/2008 | Cumming | |
| 7,806,930 B2 | 10/2010 | Brown | |
| 7,883,514 B2 | 2/2011 | Worst et al. | |
| 8,100,965 B2 | 1/2012 | Cumming et al. | |
| 8,337,550 B2 | 12/2012 | Griffis, III | |
| 2002/0116062 A1* | 8/2002 | Portney | A61F 2/1602 623/6.46 |

(Continued)

*Primary Examiner* — Leslie Lopez
(74) *Attorney, Agent, or Firm* — Warren D. Schickli; Stites & Harbison PLLC (57) ABSTRACT

An eye implant has a body including (a) a receiver, (b) a first mounting clip and (c) a second mounting clip. The receiver is adapted to hold an intraocular device to be implanted in an eye. The receiver, the first mounting clip and the second mounting clip generally extend along a common arc.

9 Claims, 6 Drawing Sheets

(56) References Cited

U.S. PATENT DOCUMENTS

| | | | | |
|---|---|---|---|---|
| 2007/0106379 A1* | 5/2007 | Messner | ............... | A61F 2/1602 |
| | | | | 623/6.51 |
| 2012/0238857 A1* | 9/2012 | Wong | .................... | A61F 2/1694 |
| | | | | 600/398 |
| 2017/0209045 A1* | 7/2017 | Choo | ........................ | A61B 3/16 |
| 2018/0369017 A1* | 12/2018 | Schieber | ................. | A61M 5/00 |

* cited by examiner

DEVICE FOR SECURING AN INTRAOCULAR DEVICE IN AN EYE

RELATED APPLICATION

This application claims priority to U.S. Provisional Patent Application Ser. No. 62/967,187 filed on Jan. 29, 2020 which is hereby incorporated by reference in its entirety.

GOVERNMENT SUPPORT

This invention was made with an award from the Kentucky Cabinet for Economic Development, under Grant Agreement CED 2019-001-004.

TECHNICAL FIELD

This document relates generally to eye implants and, more particularly, to a new and improved eye implant adapted for receiving an intraocular device and holding that intraocular device at a desired position within the eye of a patient as well as to a related implantation method.

BACKGROUND

Various intraocular devices have been developed for in situ placement in the eye in order to (a) monitor chemical and physical characteristics in the eye related to eye diseases and medical conditions and/or (b) treat those eye diseases and medical conditions. Such intraocular devices include, but are not necessarily limited to (1) physical sensors for monitoring force, pressure, acceleration, etc., (2) chemical sensors for monitoring oxygen, glucose, amino acids, electrolytes, antigens, antibodies, etc., (3) miniature cameras, (4) drug delivery systems, (5) fluid pumps and (6) combinations thereof.

Such eye diseases and medical conditions include, but are not necessarily limited to glaucoma, cataracts, diabetes, strabismus and macular degeneration.

This document relates to a new and improved eye implant configured to receive and hold an intraocular device of the type described above at a desired position within the eye of a patient as well as to a related implantation method.

SUMMARY

In accordance with the purposes and benefits described herein, a new and improved eye implant is provided comprising a curvilinear body. In one or more of the many possible embodiments of the eye implant, that body further includes a receiver adapted to receive and hold an intraocular device to be implanted in an eye. The body may further include a first mounting clip. The body may further include a second mounting clip. In one or more of the many possible embodiments, the first mounting clip and the second mounting clip may be provided at opposed ends of the body.

More specifically, the first mounting clip and the second mounting clip may be centered upon a radius of curvature $R_1$ of between about 4.2 mm and about 5.0 mm. The receiver may also be provided on the radius of curvature $R_1$ between said first mounting clip and said second mounting clip.

In one or more of the many possible embodiments of the eye implant, the body includes a first edge having a radius of curvature $R_2$. Further, the body may include a second edge having a radius of curvature $R_3$. In such an embodiment of the eye implant, $R_2<R_1<R_3$. $R_2$ may be between about 4.0 mm and about 4.8 mm. $R_3$ is between about 4.9 mm and 6.0 mm. Further, the body may have a transverse dimension between the first edge and the second edge of about 1.2-1.5 mm. The body may have a thickness $T_1$ at the first mounting clip and the second mounting clip and a thickness $T_2$ at the receiver wherein $T_1<T_2$. $T_1$ may be between about 0.17 mm 0.23 mm, and $T_2$ may be between about 0.30 mm and 0.52 mm.

In one or more of the many possible embodiments of the eye implant, the receiver comprises a socket inset in the body. In one or more of the many possible embodiments of the eye implant, the first clip comprises a first set of cooperating arms and a first clip gap between distal ends of the first set of cooperating arms. In one or more of the many possible embodiments of the eye implant, the second clip comprises a second set of cooperating arms and a second clip gap between distal ends of the second set of cooperating arms. The first mounting clip and the second mounting clip may be separated by an arc of between about 75 degrees and 180 degrees.

The intraocular device held in the receiver may be selected from a group consisting of a physical sensor (force, pressure, acceleration, etc.), a chemical sensor (oxygen, glucose, amino acids, electrolytes, antigens, antibodies, etc.), a miniature camera, a drug delivery system, a transceiver (optical, electromagnetic, ultrasonic, etc.), a fluid pump, and combinations thereof.

In accordance with an additional aspect, an eye implant is provided comprising a body including (a) a receiver adapted to receive and hold an intraocular device to be implanted in an eye, (b) a first mounting clip and (c) a second mounting clip, wherein the receiver, the first mounting clip and the second mounting clip extend along a common arc. That common arc may have a radius of curvature of between about 4.2 and about 5.0 mm, whereby when the eye implant is attached to an iris of the eye into which the eye implant is implanted, the eye implant does not cross a pupil of the eye.

In accordance with yet another aspect, an eye implant is provided comprising a curvilinear body adapted to extend about an optical axis of an eye into which the eye implant is implanted and when fixed to an iris of the eye, edges of the body are bounded by a pupil of the eye and an iridocorneal angle of an anterior chamber of the eye.

Still further, a new and improved method of implanting an eye implant into an eye of an individual, comprises: (a) making a corneal incision of the eye, (b) inserting the eye implant into the eye through the corneal incision and (c) securing the eye implant to an iris of the eye so that the eye implant does not cross a pupil of the eye thereby eliminating any need for an iridotomy or an iridectomy and ensuring the device does not interfere with vision.

In one or more embodiments, such a method also includes the step of completing the securing of the eye implant to the iris without making a second incision by extending a tool though the corneal incision. In addition, the method may include connecting the eye implant to the iris by enclavating iris tissue at two points.

The method may also include the step of positioning the eye implant so that the eye implant is bounded by an edge of the pupil and an iridocorneal angle of an anterior chamber of the eye.

The corneal incision may be a clear corneal incision used for cataract surgery. The corneal incision may be a clear corneal incision used for minimally invasive glaucoma surgery. In one or more of the many possible embodiments of the method, the corneal incision does not require suturing for closure.

In one or more of the many possible embodiments of the method, the method may include the step of positioning an intraocular device in a receiver of the eye implant prior to the inserting of the eye implant into the eye through the corneal incision. That intraocular device may be selected from a group of intraocular devices consisting of an intraocular pressure sensor, a miniature camera, a drug delivery system, an oxygen concentration sensor, an eye motion sensor, an eye chemistry sensor, and combinations thereof.

In accordance with yet another aspect, the method of implanting an eye implant into an eye of an individual comprises the steps of: (a) making a corneal incision of the eye, (b) inserting the eye implant into the eye through the corneal incision; and (c) securing the eye implant so that the eye implant is bounded by an edge of the pupil and an iridocorneal angle of an anterior chamber of the eye.

Such a method may include the step of completing the securing of the eye implant to the iris without making a second incision by extending a tool though the corneal incision.

Such a method may include the step of connecting the eye implant to the iris by enclavating iris tissue at two points.

The corneal incision may be a clear corneal incision used for cataract surgery. The corneal incision may be a clear corneal incision used for minimally invasive glaucoma surgery. In one or more of the many possible embodiments of the method, the corneal incision does not require suturing for closure.

In one or more of the many possible embodiments of the method, the method may include the step of positioning an intraocular device in a receiver of the eye implant prior to the inserting of the eye implant into the eye through the corneal incision. That intraocular device may be selected from a group of intraocular devices consisting of an intraocular pressure sensor, a miniature camera, a drug delivery system, an oxygen concentration sensor, an eye motion sensor, an eye chemistry sensor, and combinations thereof.

In the following description, there are shown and described several preferred embodiments of the eye implant and the related method of implanting an eye implant into the eye of an individual or patient. As it should be realized, the eye implant and method are capable of other, different embodiments and their several details are capable of modification in various, obvious aspects all without departing from eye implant and method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the patent specification, illustrate several aspects of the method and together with the description serve to explain certain principles thereof.

Reference will now be made in detail to the present preferred embodiments of the eye implant and method, examples of which are illustrated in the accompanying drawing figures.

DETAILED DESCRIPTION

Figure 1A:
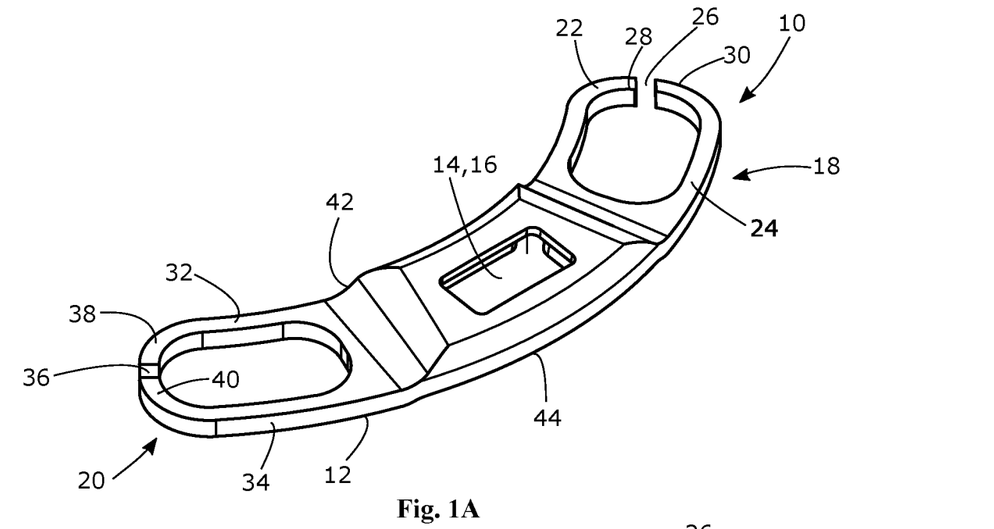
FIG. 1A is a front perspective view of the eye implant.
Figure 1B:
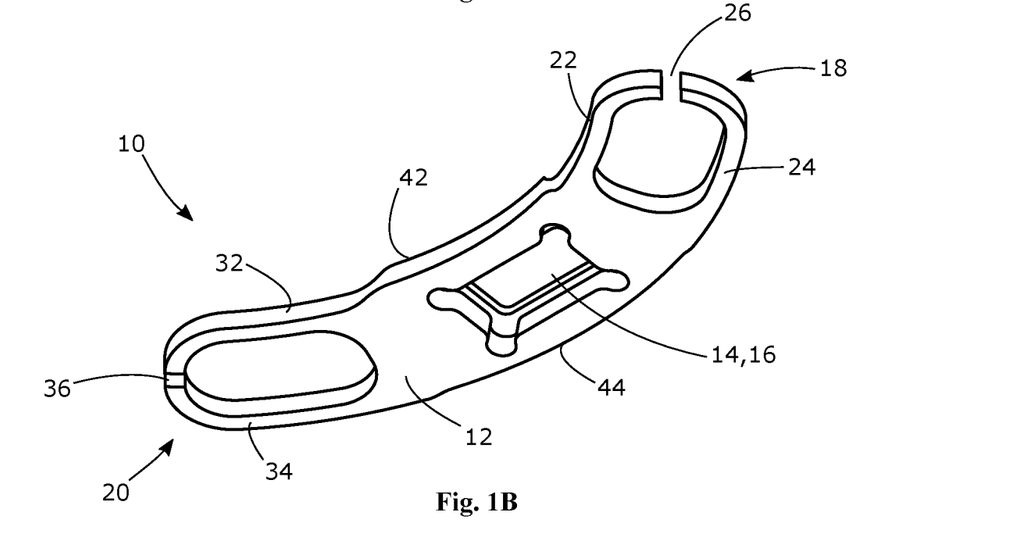
FIG. 1B is a rear perspective view of the eye implant.
Figure 1C:
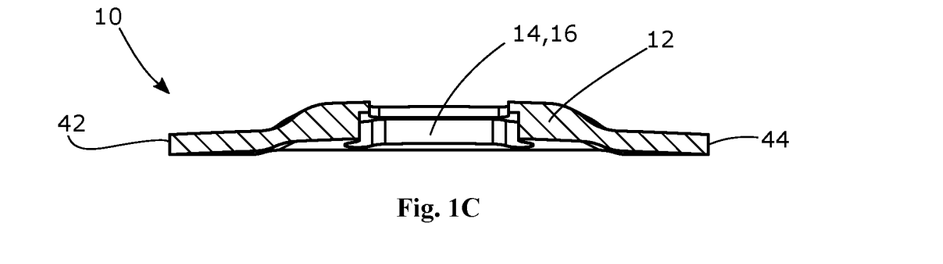
FIG. 1C is a cross sectional view of the eye implant illustrated in FIGS. 1A and 1B.
Figure 2A:
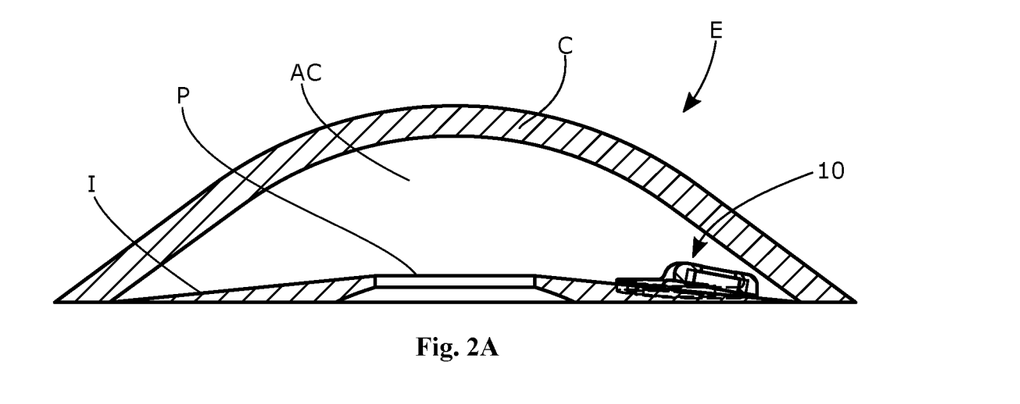
FIGS. 2A and 2B are two cross sectional views of the eye implant of FIGS. 1A-1C implanted in the anterior chamber of an eye.
Figure 2B:
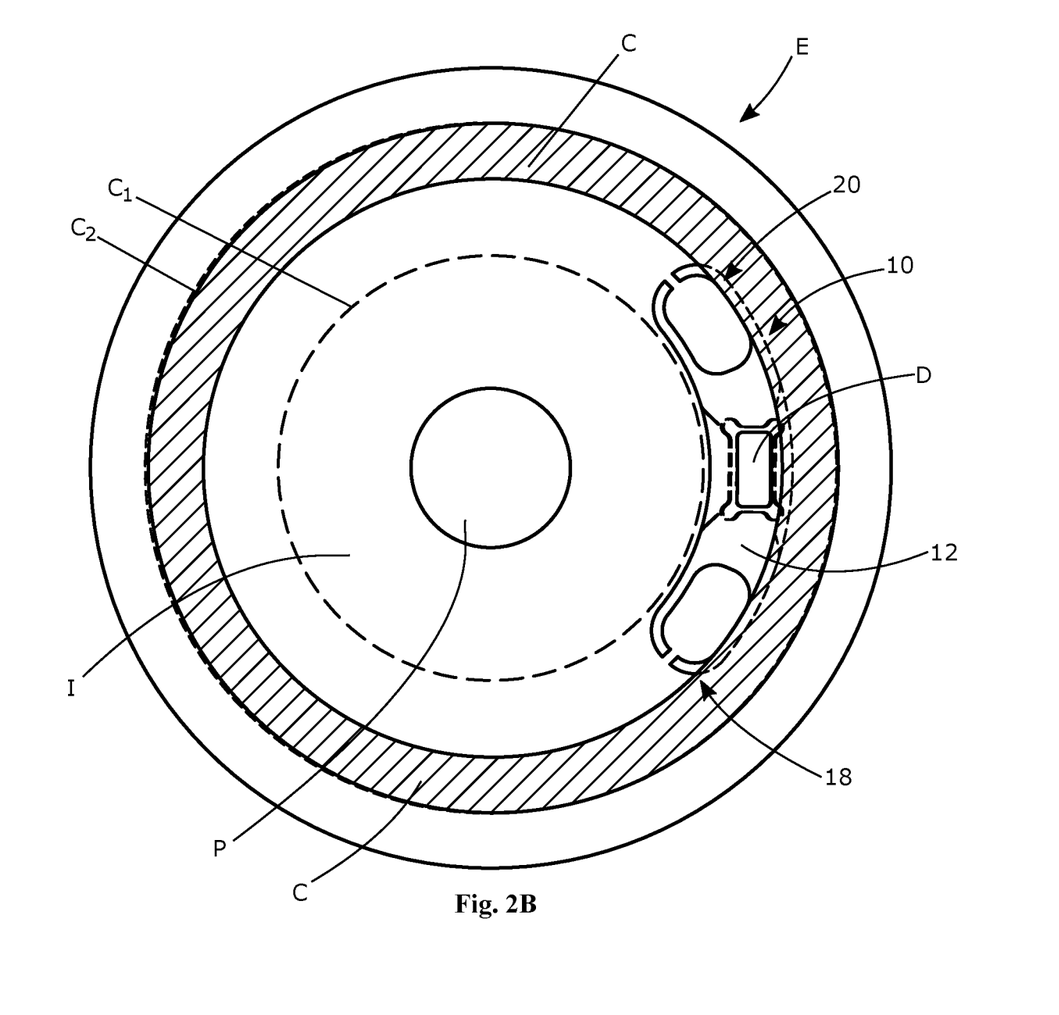

Reference is now made to FIGS. 1A-1C which illustrate the new and improved eye implant 10 having a curvilinear body 12 made from any appropriate biocompatible material. Such biocompatible material may be a biocompatible plastic, metal, metal alloy, plastic composite, ceramic or other material familiar to those skilled in the art. In one possible embodiment, the biocompatible material is a single piece of polymethylmethacrylate.

The body 12 includes a receiver 14 adapted or configured to hold an intraocular device D to be implanted in the eye of an individual or patient. More particularly, the receiver 14 may comprise a cavity, pocket or socket 16 that is inset into the body 12. The socket 16 may have one closed end. The interocular device D may comprise any of the various intraocular devices that have been developed for in situ placement in the eye in order to (a) monitor chemical and physical characteristics in the eye related to eye diseases and medical conditions and/or (b) treat those eye diseases and medical conditions. Such intraocular devices include, but are not necessarily limited to (1) a physical sensor for monitoring force, pressure, acceleration, etc., (2) a chemical sensor for monitoring oxygen, glucose, amino acids, electrolytes, antigens, antibodies, etc., (3) a miniature camera, (4) a drug delivery system, (5) a fluid pump and (6) combinations thereof. Such intraocular devices D include, but are not necessarily limited to an intraocular pressure sensor, a miniature camera, a drug delivery system, an oxygen concentration sensor, an eye motion sensor, an eye chemistry sensor, and combinations thereof.

The intraocular device D may be held in the receiver 14 or socket 16 by any appropriate means including, but not necessarily limited to, biocompatible adhesive, friction fit, interference fit, fasteners, bonding processes and combinations thereof.

The body 12 further includes a first mounting clip 18 and a second mounting clip 20. As illustrated, the first and second mounting clips 18, 20 are provided at opposed longitudinal ends of the body 12. The first mounting clip 18 and the second mounting clip 20 may be separated by an arc of between about 75 degrees to about 180 degrees. In other embodiments, the first mounting clip 18 and the second mounting clip 20 are separated by an arc of between about 75-150 degrees, between about 75-120 degrees, between about 90 and 150 degrees and between about 90 and 120 degrees.

More specifically, the first mounting clip 18 includes a first set of cooperating arms 22, 24. A first gap 26 is provided between the respective distal ends 28, 30 of the two arms 22, 24. That first gap 26 has a width of between about 0.1-0.3 mm. The second mounting clip 20 includes a second set of cooperating arms 32, 34. A second gap 36 is provided between the respective distal ends 38, 40 of the two arms 32, 34. That second gap 36 also has a width of between about 0.1-0.3 mm. In some embodiments, the first and second gaps have a width of about 0.2 mm.

In one possible embodiment of the eye implant 10, the entire body 12, including the arms 22, 24 and 32, 34 are manufactured as a single piece of biocompatible material such as polymethylmethacrylate. In other embodiments, the arms 22, 24 and 32, 34 are made from a different biocompatible material than the remainder of the body 12 including the receiver 14.

Figure 6A:
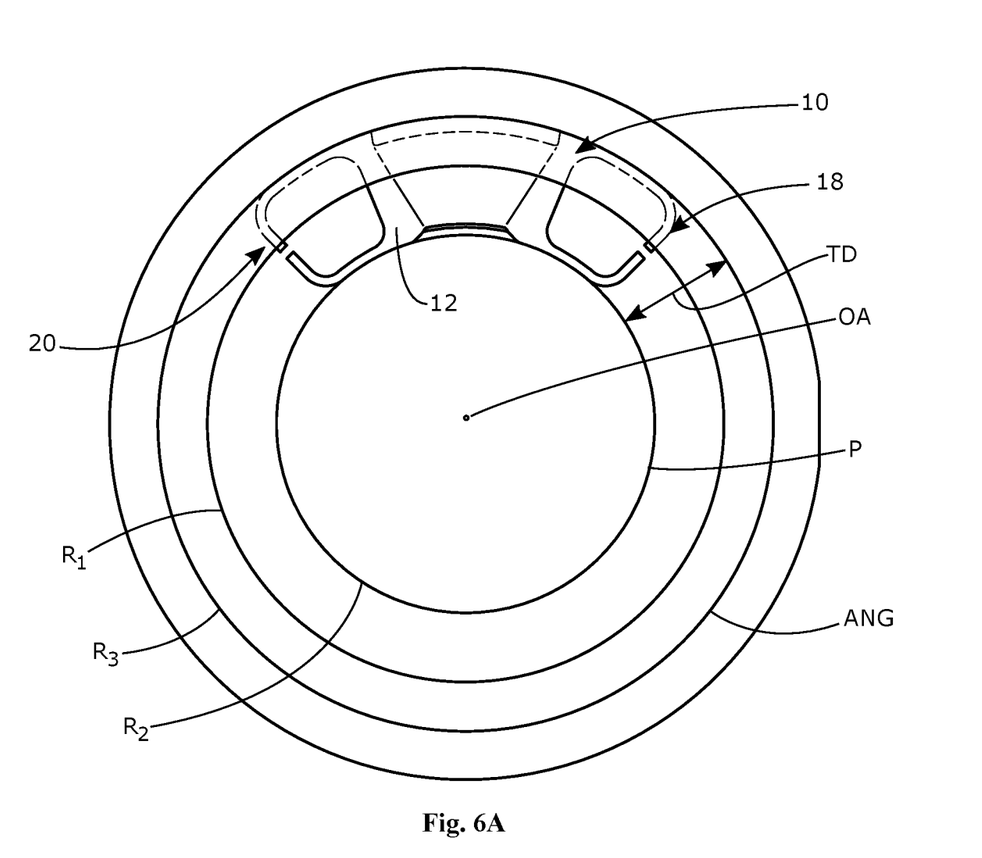
FIGS. 6A and 6B are schematic illustrations of the radius of curvature of various structural features of the implant device as related to the structure of the eye into which the eye implant is implanted.

As best appreciated from viewing FIG. 6A, the first mounting clip 18 and the second mounting clip 20 are centered upon a radius of curvature $R_1$ of between about 4.2 mm and about 5.0 mm. The radius of curvature $R_1$ approximately corresponds to a longitudinal midline L of the body 12. As also shown in FIG. 6A, the receiver 114 or socket 16 is also on the radius of curvature $R_1$ between the first mounting clip 18 and the second mounting clip 20. The receiver 14 or socket 16 may be slightly offset from the longitudinal midline L as shown or centered on that midline if desired. Thus, it should be appreciated that in multiple embodiments of the eye implant 10, the first mounting clip 18, the second mounting clip 20 and the receiver 14 all extend along a common arc, $R_1$.

The body 12 also includes a first edge 42 having a radius of curvature $R_2$ of between about 4.0-4.8 mm and a second edge 44 having a radius of curvature $R_3$ of between about 4.9 mm and 6.0 mm. Thus, $R_2 < R_1 < R_3$. As best illustrated in FIG. 6A, the first, second and third radius of curvatures $R_1$, $R_2$, $R_3$ are concentric or approximately concentric with $R_2$ substantially corresponding to the inner radius of the iris I or outer radius of the pupil P at full dilation and $R_3$ substantially corresponding to or being slightly less than the radius of the iridocorneal angle of the anterior chamber ANG.

The curvilinear body 12 is adapted to extend about the optical axis OA of the eye E into which the eye implant 10 is implanted and when fixed to the iris I of the eye, the edges 42, 44 of the body 12 are bounded by the pupil P of the eye and an iridocorneal angle ANG of an anterior chamber AC of the eye (see FIGS. 2A, 2B, 6A and 6B). As a result, the eye implant 10 does not cross the pupil P of the eye E into which the eye implant is implanted. In fact, when the eye implant 10 is properly implanted and positioned in the eye E of an individual or patient, the center point for measuring the radius of curvatures $R_1$, $R_2$ and $R_3$ substantially corresponds to the optical axis OA of the eye.

As best illustrated in FIG. 6A, the body 12 has a transverse dimension TD between the first edge 42 and the second edge 44 of about 1-2-1.5 mm. The body 12 also has a thickness $T_1$ at the first and second mounting clips 18, 20 and a thickness $T_2$ at the receiver 14 or socket 16 wherein $T_1 < T_2$. In one possible embodiment, $T_1$ is between about 0.17-0.23 mm and $T_2$ is between about 0.3-0.52 mm.

As should be appreciated, the curvilinear shape and dimensions of the body 12 are chosen such that the body does not interfere with the pupil P and does not contact the cornea C when properly implanted in an eye. The outer or second edge 44 may be rounded to increase the clearance for the cornea C and prevent damage to the inner surface of the cornea in case of contact.

The inner or first edge 42 is on a circle larger than the diameter of the pupil P at full dilation. The dimensions of the flexible arms 22, 24, and 32, 34 and the curvature of the body 12 are chosen to reduce contact with the iris I while still stabilizing the device 10 against rotation that may otherwise lead to cornea contact. It should be appreciated that the gaps 26, 36 are located on a circle centered on the pupil P and crossing through the middle of the body 12. This placement of the gaps 26, 36 provides an equal stiffness for each arm 22, 24 and 32, 34 and reduces tilting.

Figure 3A:
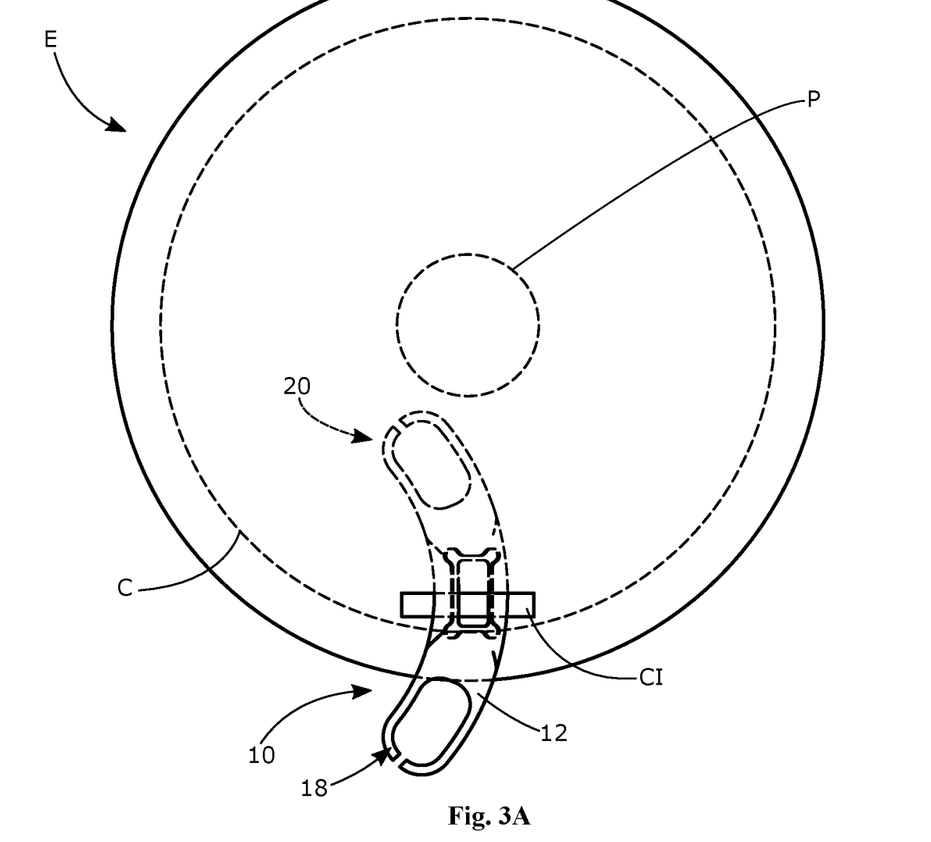
FIG. 3A illustrates the eye implant of FIGS. 1A-1C being implanted into the anterior chamber of an eye through a clear corneal incision.
Figure 3B:
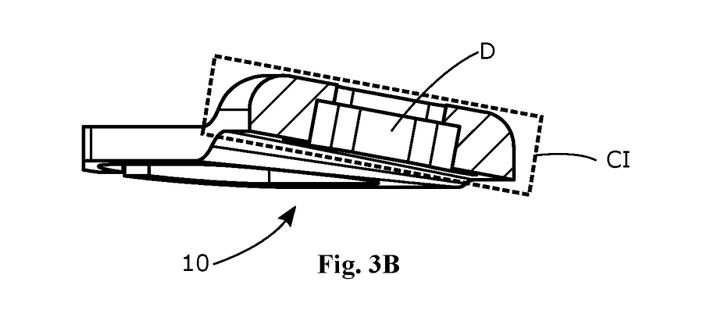
FIG. 3B is a cross sectional view showing the eye implant passing through the corneal incision.
Figure 3C:
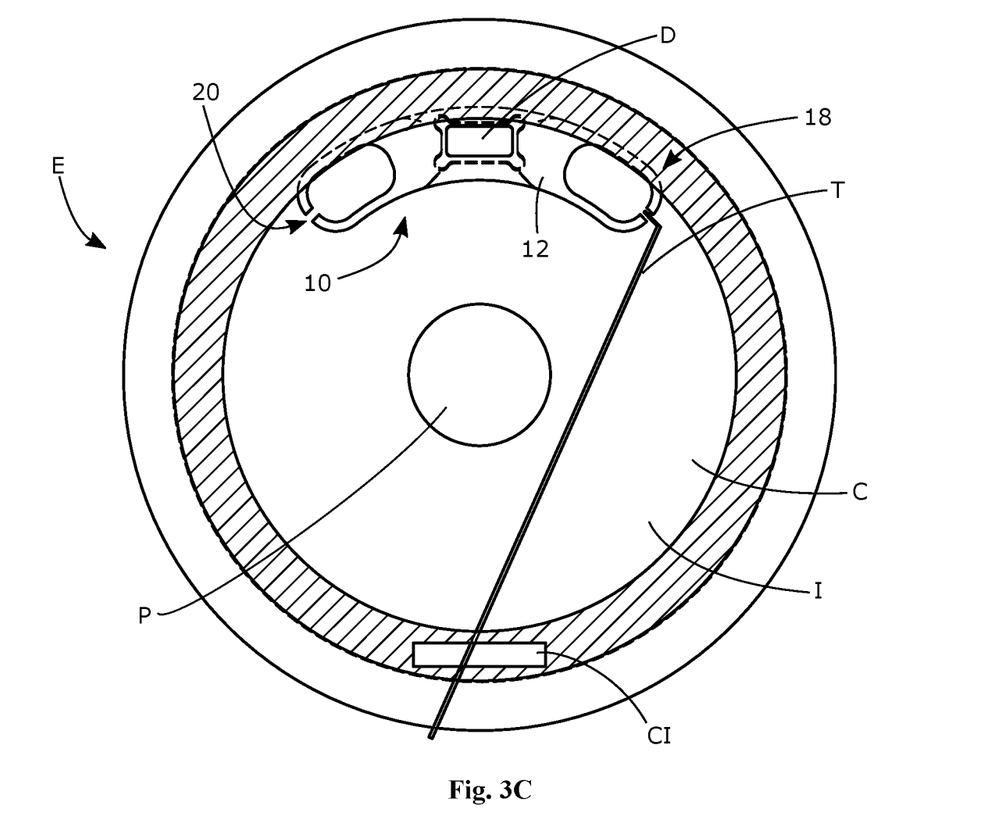
FIG. 3C is yet another cross sectional view of the eye implant illustrating iris enclavation using a tool inserted through the same incision used to pass the eye implant into the anterior chamber.

Reference is now made to FIGS. 3A-3C which illustrate the new and improved method of implanting an eye implant 10 into an eye E of an individual or patient. That method may be broadly described as including the steps of making a corneal incision CI of the eye E, inserting the eye implant 10 into the eye through the corneal incision (see FIGS. 3A and 3B) and securing the eye implant to the iris I of the eye so that the eye implant does not cross the pupil of the eye, thereby eliminating any need for an iridotomy or an iridectomy and not interfering with vision.

The corneal incision CI may be a clear corneal incision of the type used for cataract surgery or a clear corneal incision of the type used for minimally invasive glaucoma surgery. Advantageously, such a corneal incision CI does not require suturing for closure. FIG. 3A illustrates the eye implant 10 being implanted through the corneal incision CI into the anterior chamber AC of the eye E.

Figure 4:
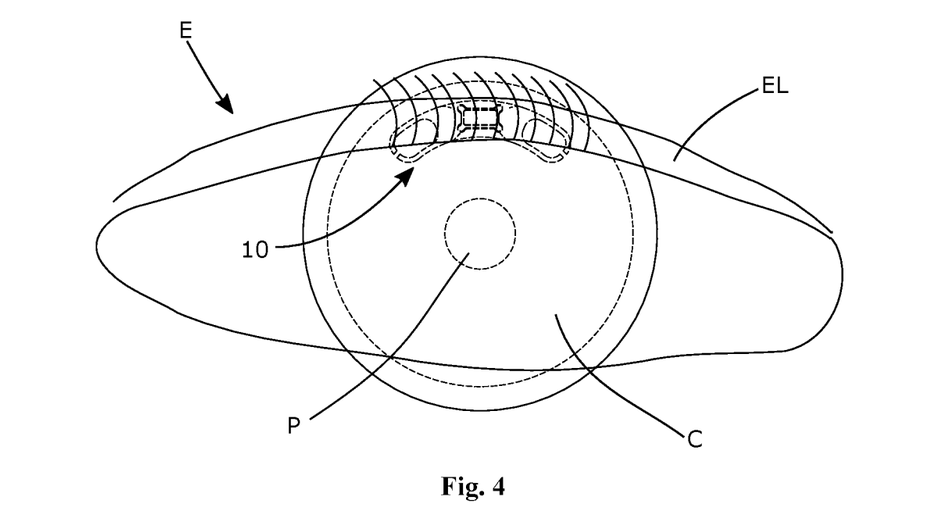
FIG. 4 is a view illustrating how the implanted eye implant can be almost completely obscured behind a relaxed eye lid.
Figure 5A:
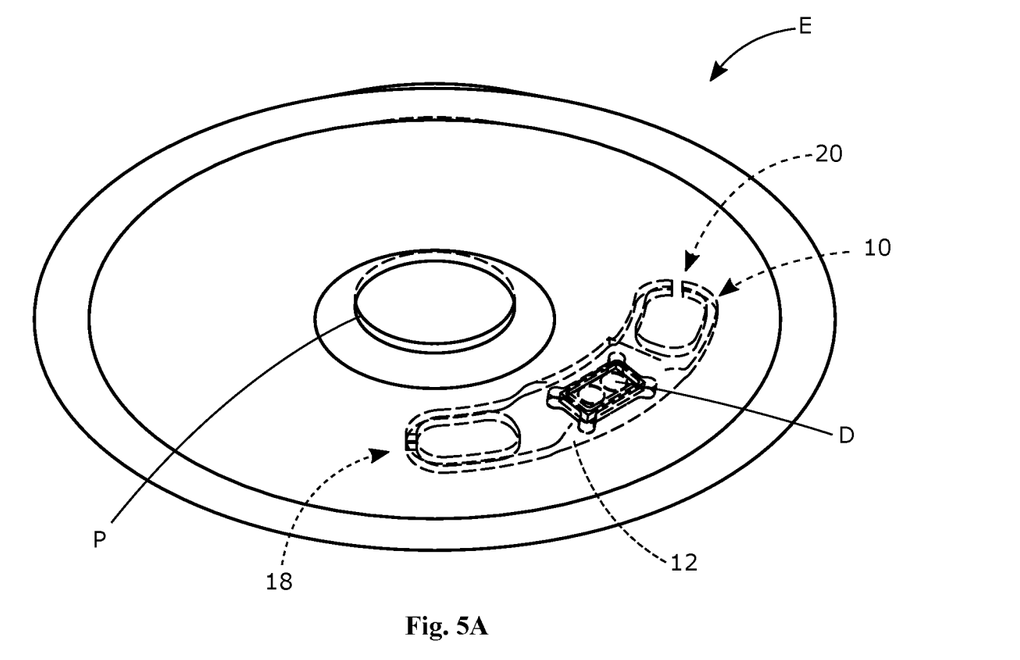
FIGS. 5A and 5B are respective isometric and cross sectional views of the implanted eye implant holding an intraocular device at a desired angle with respect to the cornea.
Figure 5B:
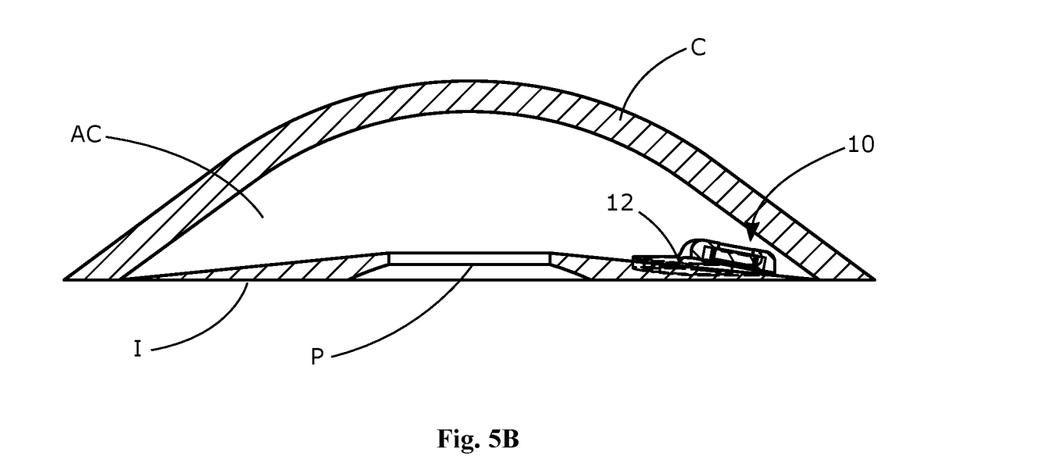

As illustrated in FIG. 3C, this securing can be done by extending a tool T through the corneal incision CI. As a result, the securing of the eye implant 10 to the iris I can be completed without making a second incision. More specifically, FIG. 3C shows the iris I being enclavated in the gap 26 using the tool T. In one embodiment, illustrated in FIG. 4, the eye implant 10 is covered by the eyelid EL when the eyelid is in the open and relaxed state. However, implantation at other positions in the eye may be preferable depending on the application and surgical considerations.

More particularly, the securing may include connecting the eye implant 10 to the iris I by enclavating iris tissue at two points: that is in the first and second gaps 26 and 36 between the respective first and second sets of cooperating arms 22,24 and 32,34 of the first and second mounting clips 18, 22. The points on the iris I selected for enclaving do not move during dilation and constriction of the pupil P.

The dimensions of the gaps 26, 36 are chosen to enclavate sufficient iris tissue with the sufficient force to secure the eye implant 10 without perforating the iris. The dimensions of the arms 22, 24 and 32, 34 are chosen to reduce contact with portions of the iris I which move slightly during dilation and constriction.

It should be appreciated that the arms 22, 24 and 32, 34 are sufficiently flexible to be manipulated with the tool T during ocular surgery and sufficiently stiff to hold the iris tissue. This balance is achieved by choosing an appropriate material for the construction of the arms and adjusting the shape and dimensions of the arms. In one possible embodiment, the arms 22, 24 and 32, 34 are made from polymethylmethacrylate and have square cross-sections of 0.2×0.2 mm. Other materials and geometries may be used to achieve the desired flexibility and folding force.

Figure 6B:
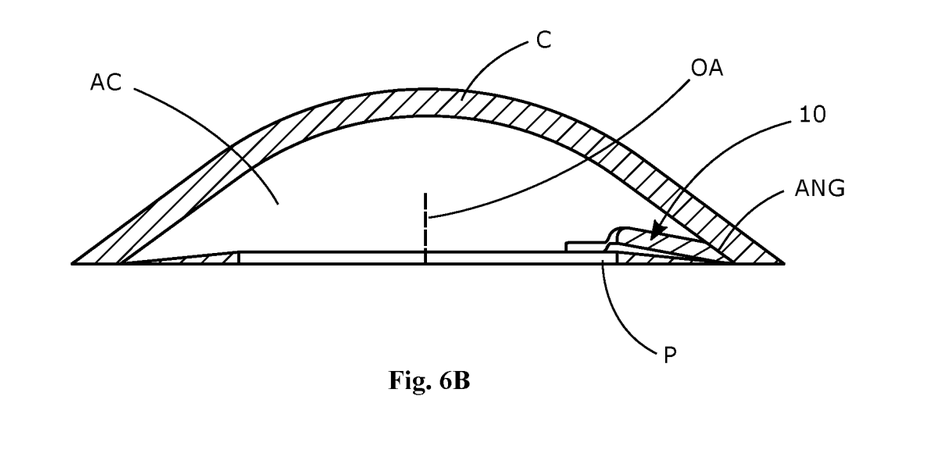

The method may also include the step of positioning the eye implant 10 so that the eye implant is bounded by an edge of the pupil P and an iridocorneal angle ANG of an anterior chamber AC of the eye (see FIGS. 6A and 6B).

Of course, the method may also include the step of positioning an intraocular device in the receiver 14 of the eye implant device 10 prior to inserting the eye implant device into the eye E through the corneal incision CI. Further, the method may include selecting the intraocular device from a group of intraocular devices consisting of (a) a physical sensor, a chemical sensor, a miniature camera, a drug delivery system, a transceiver (optical, electromagnetic, ultrasonic, etc.), a fluid pump, and combinations thereof or (b) an intraocular pressure sensor, a miniature camera, a drug delivery system, an oxygen concentration sensor, an eye motion sensor, an eye chemistry sensor, and combinations thereof.

The new and improved method may also be broadly described as including the steps of: (a) making a corneal incision CI of the eye E, (b) inserting the eye implant 10 into the eye through the corneal incision; and (c) securing the eye implant so that the eye implant is bounded by an edge of the pupil P and an iridocorneal angle ANG of an anterior chamber AC of the eye. When properly implanted, the body 12 of the eye implant 10 is delimited by two concentric circles $C_1$ and $C_2$ centered on the center of the pupil P (see FIG. 2B).

Such a method may include the step of completing the securing of the eye implant 10 to the iris I without making a second incision by extending a tool T though the corneal incision. Such a method may include the step of connecting the eye implant 10 to the iris I by enclavating iris tissue at two points as described above.

The corneal incision may be a clear corneal incision CI of the type used for cataract surgery. The corneal incision CI may be a clear corneal incision of the type used for minimally invasive glaucoma surgery. In one or more of the many possible embodiments of the method, the corneal incision CI does not require suturing for closure.

In one or more of the many possible embodiments of the method, the method may include the step of positioning an intraocular device D in a receiver 14 of the eye implant 10 prior to the inserting of the eye implant into the eye E through the corneal incision CI. That intraocular device D may be selected from a group of intraocular devices consisting of (a) a physical sensor (force, pressure, acceleration, etc.), a chemical sensor (oxygen, glucose, amino acids, electrolytes, antigens, antibodies, etc.), a miniature camera, a drug delivery system, a transceiver (optical, electromagnetic, ultrasonic, etc.), a fluid pump, and combinations thereof or (b) an intraocular pressure sensor, a miniature camera, a drug delivery system, an oxygen concentration sensor, an eye motion sensor, an eye chemistry sensor, and combinations thereof.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of". Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms concentric, parallel or perpendicular are meant to mean approximately meeting this condition, unless otherwise specified.

It is to be fully understood that certain aspects, characteristics, and features, of the eye implant and method, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the eye implant and method which are illustratively described and presented in combination or sub-combination in the context or format of a single embodiment may also be illustratively described and presented in the context or format of a plurality of separate embodiments.

Although the eye implant and method of this disclosure have been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed. Obvious modifications and variations are possible in light of the above teachings. For example, the body 12 may include more than one receiver 14 for holding more than one intraocular device D. The body 12 may also include more than two mounting clips 18, 20 or clips with more than two arms 22, 24 and 32, 34. All such modifications and variations are within the scope of the appended claims when interpreted in accordance with the breadth to which they are fairly, legally and equitably entitled.

What is claimed:

1. An eye implant, comprising a curvilinear body including (a) a receiver adapted to receive and hold an intraocular device to be implanted in an eye, (b) a first mounting clip and (c) a second mounting clip wherein (i) the first mounting clip and the second mounting clip are adapted to enclavate iris tissue to secure the eye implant without perforating the iris tissue and (ii) the eye implant is adapted so that the curvilinear body and the intraocular device held therein do not extend across the pupil and an optical axis of the eye in which the eye implant is implanted when fixed in position by the first and second mounting clips wherein (a) the first mounting clip and the second mounting clip open away from the receiver, (b) the first mounting clip and the second mounting clip are provided at opposed ends of said body, (c) the first mounting clip and the second mounting clip are centered upon a radius of curvature R1 of between about 4.2 mm and about 5.0 mm, (d) the receiver is also on said radius of curvature R1 between said first mounting clip and said second mounting clip, (e) the body includes a first edge having a radius of curvature R2, (f) the body includes a second edge having a radius of curvature R3, and (g) R2<R1<R3.

2. The eye implant of claim 1, wherein R2 is between about 4.0 mm and about 4.8 mm.

3. The eye implant of claim 2, wherein R3 is between about 4.9 mm and about 6.0 mm.

4. The eye implant of claim 1, wherein the body has a transverse dimension between a first edge and a second edge of about 1.2 mm to about 1.5 mm.

5. He eye implant of claim 4, wherein the body has a thickness T1 at the first mounting clip and the second mounting clip and a thickness T2 at the receiver wherein T1<T2.

6. The eye implant of claim 5, wherein T1 is between about 0.17 mm and about 0.23 mm, and T2 is between about 0.30 mm and about 0.52 mm.

7. The eye implant of claim 1, wherein the first mounting clip comprises a first set of cooperating arms and a first clip gap between distal ends of the first set of cooperating arms.

8. The eye implant of claim 7, wherein the second mounting clip comprises a second set of cooperating arms and a second clip gap between distal ends of the second set of cooperating arms.

9. The eye implant of claim 1, wherein the first mounting clip and the second mounting clip are separated by an arc of between about 75 degrees and about 180 degrees.

* * * * *